(12) United States Patent
Strober et al.

(10) Patent No.: US 9,504,715 B2
(45) Date of Patent: Nov. 29, 2016

(54) ENHANCEMENT OF ALLOGENEIC HEMATOPOIETIC STEM CELL TRANSPLANTATION

(71) Applicant: THE BOARD OF TRUSTEES OF THE LELAND STANFORD JUNIOR UNIVERSITY, Stanford, CA (US)

(72) Inventors: Samuel Strober, Stanford, CA (US); Suparna Dutt, Palo Alto, CA (US); Robert Lowsky, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/686,646

(22) Filed: Apr. 14, 2015

(65) Prior Publication Data
US 2015/0216900 A1  Aug. 6, 2015

Related U.S. Application Data

(63) Continuation of application No. 13/347,452, filed on Jan. 10, 2012, now abandoned.

(60) Provisional application No. 61/460,981, filed on Jan. 10, 2011.

(51) Int. Cl.
| | |
|---|---|
| *A01N 63/00* | (2006.01) |
| *A61K 35/17* | (2015.01) |
| *A61K 35/28* | (2015.01) |
| *C12N 5/0783* | (2010.01) |

(52) U.S. Cl.
CPC .............. *A61K 35/17* (2013.01); *A61K 35/28* (2013.01); *C12N 5/0637* (2013.01)

(58) Field of Classification Search
None
See application file for complete search history.

(56) References Cited

U.S. PATENT DOCUMENTS

| | | | |
|---|---|---|---|
| 6,143,292 A | 11/2000 | Slavin | |
| 2004/0228848 A1 | 11/2004 | Har-Noy | |

FOREIGN PATENT DOCUMENTS

| | | |
|---|---|---|
| EP | 1123384 | 4/2004 |
| JP | 2013-537187 | 9/2013 |
| WO | 2010049935 | 5/2010 |
| WO | 2012/032526 | 3/2012 |

OTHER PUBLICATIONS

Baron et al., Immunity, 18:193-204 (2003).*
Alpdogan; et al., "Interleukin-15 enhances immune reconstitution after allogeneic bone marrow transplantation", Blood (2005), 105(2):865-873.
Alpdogan; et al., "Interleukin-15 enhances immune reconstitution after allogeneic bone marrow transplantation", 9MED (2006), abstract, 11 pages, http://journal.9med.net/qikan/article.php?id=187487.
Zangi; et al., "Direct Imaging of Immune Rejection and Memory Induction by Allogeneic Mesenchymal Stromal Cells", Stem Cells (2009), 27:2865-2874.
Zhang; et al., "Effects of allogeneic hematopoietic stem cell transplantation plus thymus transplantation on malignant tumors: comparison between fetal, newborn, and adult mice", Stem Cells and Development (2011), 20(4):599-607.
Database Biosis [Online] Biosciences Information Service, Philadelphia, PA, US; Nov. 2010, Lask Assaf et al.: Ex Vivo Generated Donor Central Memory CD8 T Cells, Previously Shown to Enhance Engraftment of Allogeneic Bone Marrow, Also Exhibit Significant GVL Activity without Causing Gvhd in an In Vivo b Cell Lymphoma Model.
Fowler et al., "Non-host-reactive donor CD8+ T cells of Tc2 phenotype potently inhibit marrow graft rejection", Blood (1998) 91(11):4045-50.
Dutt et al., Memory phenotype CD8+T cells are superior to naive CD8+ T cells in separating graft anti-tumor activity from GVHD after bone marrow transplantation: Application to DLI, ASH poster and abstract (2009).
Zhang et al., Donor CD8+ T Cells Mediate Graft-versus-Leukemia Activity without Clinical Signs of Graft-versus-Host Disease in Recipients Conditioned with Anti-CD3 Monoclonal Antibody, J. Immunol., 178:838-850 (2007).
Liang et al., Donor CD8+ cell facilitate induction of chimerism and tolerance without GVHD in autoimmune NOD mice conditioned with andi-CD3 mAb, Blood, 1 05(5):2180-2188 (2005).
Machura et al., Expression of naive/memory (CD45RA/CD45RO) markers by peripheral blood CD4+ and CD8+ T cells in children with asthma, Arch. Immunol. Ther. Exp., vol. 56:55-62 (2008).
Zhang et al., Host-reactive CD8+ memory stem cells in graft-versus-host disease, Nature Medic., vol. 11, No. 12 1299-1305 (2005).
Chen et al., Inability of memory T cells to induce graft-versus-host disease is a result of an abortive alloresponse, Blood, vol. 109, No. 7, pp. 3115-3123 (2007).
Riddell et al., Graft-Versus-Host Disease: A Surge of Developments, PLoS Medic., vol. 4, Issue 7, pp. 1174-1177 (2007).

(Continued)

*Primary Examiner* — Thomas J Visone
(74) *Attorney, Agent, or Firm* — Pamela J. Sherwood; Bozicevic, Field & Francis LLP

(57) ABSTRACT

Methods and compositions are provided to augment the conversion of mixed hematopoietic cell chimerism to complete donor cell chimerism following allogeneic hematopoietic cell transplantation (HCT), where such transplantation may be utilized for treatment of cancer such as leukemia and lymphoma or for other conditions requiring reconstitution of the hematopoietic system, e.g. treatment of anemias, thalassemias, autoimmune conditions, and the like. The present invention improves on conventional DLI by utilizing a composition of substantially purified donor memory $CD8^+$ T cells as DLI following allogeneic HCT, where the cells are administered at a suitable time following transplantation. The methods provide for a more complete donor chimerism, and have the further benefit of killing tumor cells without GVHD. The memory CD8+ T cells may include one or both of central and effector memory T cells, usually both.

12 Claims, 7 Drawing Sheets
(3 of 7 Drawing Sheet(s) Filed in Color)

(56) References Cited

OTHER PUBLICATIONS

Zhang et al., Dendritic cell-activated CD44 hi CD8+ T Cells are defective in mediating acute graft-versus-host disease but retain graft-versus-leukemia activity, Blood, vol. 103, No. 10, pp. 3970-3978 (2004).

Lichtman et al., CD45RA−RO+ (Memory) but Not CD45RA+RO− (Naive) T Cells Roll Efficientrly on E- and P-Selectin and Vascular Cell Adhesion Molecule-1 Under Flow, J. I mmunol., 158: 3640-3650 (1997).

Zhang et al., Donor CD8+T Cells Mediate Graft-versus-Leukemia Activity without clinical signs of Graft-versus-Host Disease in Recipients Conditioned with Anti-CD3 Monoclonal Antibody, J. Immunol., 1778:838-850 (2007).

Maldonado et al., Decreased effector memory CD45RA+CD62L−CD8+ T cells and increased central memory CD45RA−CD62L+CD8+ T Cells in peripheral blook of rheumatoid arthritis patients, (Arthritis Res. Ther., vol. 5., No. 2, R91-R96 (2003).

Suzuki et al., "Are CD8 +CD122+ cells regulatory T cells or memory T cells?", Human Immunology, Sep. 24, 2008, pp. 751-754, Elsevier, Atlanta, GA.

Tough, "Deciphering the relationship between central and effector memory CD8+ T cells", Trends in Immunology, Aug. 2003, pp. 404-407,vol. 24, No. 8, Elsevier, Atlanta, GA.

\* cited by examiner

ENHANCEMENT OF ALLOGENEIC HEMATOPOIETIC STEM CELL TRANSPLANTATION

GOVERNMENT RIGHTS

This invention was made with Government support under contract CA049605 awarded by the National Institutes of Health. The Government has certain rights in the invention.

BACKGROUND OF THE INVENTION

Cancer, also known as malignant neoplasm, is characterized by an abnormal growth of cells that display uncontrolled cell division, invasion and destruction of adjacent tissues, and sometimes metastasis to other locations in the body. There are more than 100 types of cancer, including breast cancer, skin cancer, lung cancer, colon cancer, prostate cancer, and lymphoma. Cancer is the second leading cause of death in America and it causes about 13% of all deaths. Cancer may affect people at all ages, even fetuses, but the risk for most types of cancer increases with age. Cancers can affect all animals.

Chemotherapy has become the standard of care for many cancers. Chemotherapy refers to antineoplastic drugs used to treat cancer or the combination of these drugs into a cytotoxic standardized treatment regimen. Most commonly, chemotherapy acts by killing cells that divide rapidly, one of the main properties of cancer cells. This means that it also harms cells that divide rapidly under normal circumstances: cells in the bone marrow, digestive tract and hair follicles; this results in the most common side effects of chemotherapy-myelosuppression (decreased production of blood cells), mucositis (inflammation of the lining of the digestive tract) and alopecia (hair loss). Newer anticancer drugs act directly against abnormal proteins in cancer cells; this is termed targeted therapy.

Allogeneic hematopoietic cell transplantation (HCT) can be curative for patients with leukemia and lymphomas, especially if the recipient is in complete remission at the time of transplantation. However, the risk of progressive disease or of relapse is considerably greater if the recipient is in partial remission at the time of transplantation, or if mixed rather than complete chimerism develops when non-myeloablative conditioning is used.

Despite these new agents and improved combinations, the current treatment is still not effective for many types of cancers or cancers at different stages. Improved regimens and treatments are greatly needed for cancer therapy.

SUMMARY OF THE INVENTION

In one embodiment of the invention, compositions and methods are provided for augmenting the treatment of cancer, including without limitation leukemias and lymphomas, after allogeneic hematopoietic cell transplantation by adding a purified subset of donor lymphocytes that can kill the tumor cells without inducing the major complication of graft versus host disease (GVHD).

In a related embodiment, methods and compositions are provided to augment the conversion of mixed hematopoietic cell chimerism to complete donor cell chimerism following allogeneic hematopoietic cell transplantation (HCT), where such transplantation may be utilized for treatment of cancer or for other conditions requiring reconstitution of the hematopoietic system, e.g. treatment of anemias, thalassemias, autoimmune conditions, and the like. Mixed chimerism is associated with a much higher rate of cancer progression or relapse compared to patients who achieve full donor chimerism by following allogeneic HCT. Although donor lymphocyte infusions (DLI) may be conventionally given at a time point after transplantation, DLI is ordinarily made up of peripheral blood mononuclear cells that contain all subsets of T cells in the blood and thus carries a major risk of inducing severe GVHD.

The present invention improves on conventional DLI by utilizing a composition of substantially purified donor memory $CD8^+$ T cells as DLI following allogeneic HCT, where the cells are administered at a suitable time following transplantation in humans, e.g. from about 2 to about 6 months to prevent tumor relapse or at the time of tumor relapse to treat the relapse. The methods provide for a more complete donor chimerism, and have the further benefit of killing tumor cells. The memory CD8+ T cells may include one or both of central and effector memory T cells, usually both. The donor memory T cells are generally purified, and may be selected for with an affinity agent specific for CD8, alone or in combination with other markers of such cells as known in the art, including without limitation a $CD8^+$ $CD44^+$ population. The T cells are administered in a dose effective to promote complete chimerism and, when appropriate, to enhance killing of tumor cells.

In some embodiments, the cancer is a solid tumor. Examples of solid tumors that can be treating using the subject methods of the present invention include but are not limited to colorectal cancer, lung cancer, breast cancer, pancreatic cancer, liver cancer, prostate cancer, and ovarian cancer. In other embodiments, the cancer is a leukemia or lymphoma, including without limitation, acute lymphocytic leukemia (ALL), acute myelogenous leukemia (AML), chronic myelogenous leukemia (CML), lymphomas such as Hodgkin and non-Hodgkin lymphomas, etc. In some embodiments, the tumor cells are a primary or metastatic tumor.

BRIEF DESCRIPTION OF THE DRAWINGS

The patent or application file contains at least one drawing executed in color. Copies of this patent or patent application publication with color drawings will be provided by the United States Patent and Trademark Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings.

DETAILED DESCRIPTION OF THE EMBODIMENTS

Figure 1:
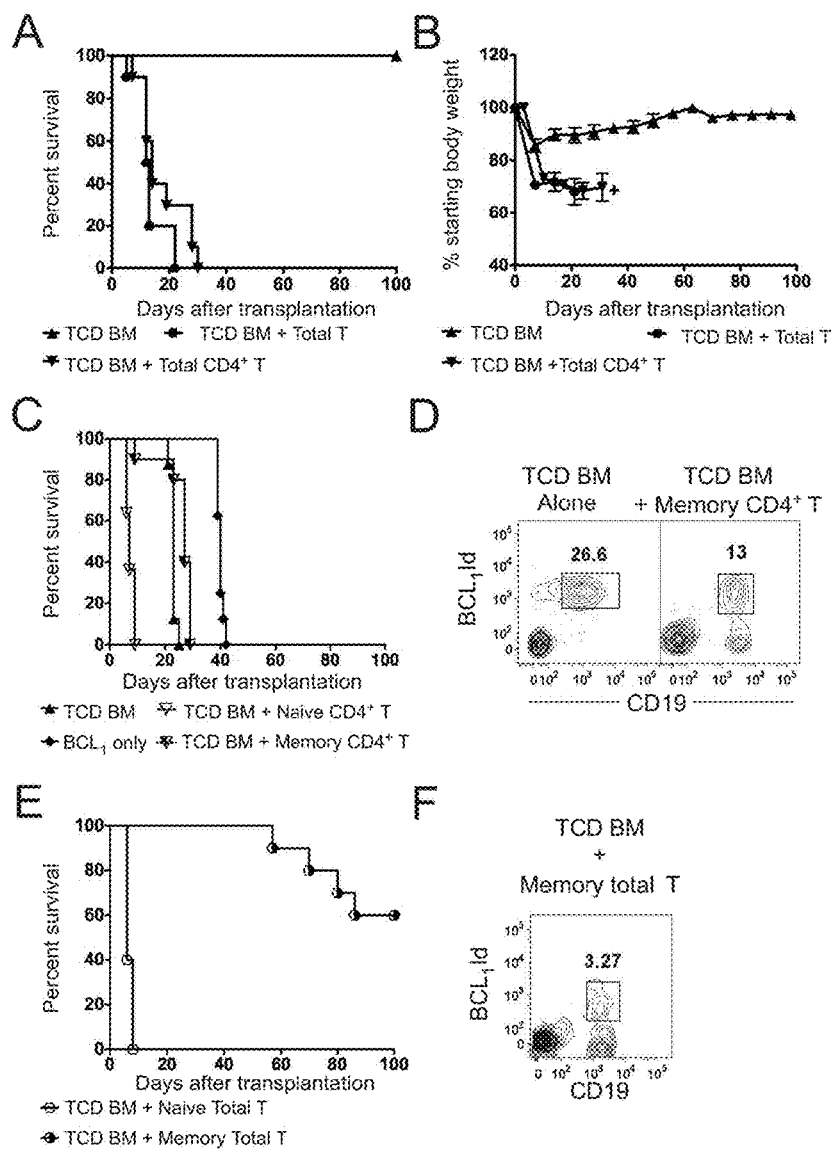
FIG. 1. Survival of BALB/c hosts transplanted with donor C57BL/6 TCD BM cells with or without total T or T cell subsets. A, Lethally irradiated (800 cGy) hosts were given $2\times10^6$ TCD BM cells from donors with or without (N=12) O. $5\times10^6$ sorted donor total T (N=10) or total $CD4^+$ T (N=10) cells from the spleen. The data were pooled from two independent experiments. B, Serial measurements of body weights were determined in mice from panel A. +Weight measurements were stopped when no more than 2 mice remained in the group. C, The hosts received 500 $BCL_1$ lymphoma cells 6 hours after irradiation. Lethally irradiated hosts were given $2\times10^6$ TCD BM cells with or without (N=8) $0.5\times10^6$ sorted $CD62L^{hi}CD44^{lo}$ naive (N=10) or $CD44^{hi}$ memory phenotype $CD4^+$ T cells (N=10). Control untreated hosts were given tumor cells also (N=8). The data were pooled from two independent experiments. D and F, Representative two-color flow cytometric analyses of CD19 versus $BCL_1$-idiotype markers in the peripheral blood from recipients with progressive tumor growth in C and E respectively are shown 28 days after transplant of TCD BM alone or with memory $CD4^+$ T cells or memory total T cells respectively.

To facilitate an understanding of the invention, a number of terms are defined below.

Before the present active agents and methods are described, it is to be understood that this invention is not limited to the particular methodology, products, apparatus and factors described, as such methods, apparatus and formulations may, of course, vary. It is also to be understood that the terminology used herein is for the purpose of describing particular embodiments only, and is not intended to limit the scope of the present invention which will be limited only by appended claims.

It must be noted that as used herein and in the appended claims, the singular forms "a," "and," and "the" include plural referents unless the context clearly dictates otherwise. Thus, for example, reference to "a drug candidate" refers to one or mixtures of such candidates, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Generally, conventional methods of protein synthesis, recombinant cell culture and protein isolation, and recombinant DNA techniques within the skill of the art are employed in the present invention. Such techniques are explained fully in the literature, see, e.g., Maniatis, Fritsch & Sambrook, Molecular Cloning: A Laboratory Manual (1982); Sambrook, Russell and Sambrook, Molecular Cloning: A Laboratory Manual (2001); Harlow, Lane and Harlow, Using Antibodies: A Laboratory Manual: Portable Protocol No. I, Cold Spring Harbor Laboratory (1998); and Harlow and Lane, Antibodies: A Laboratory Manual, Cold Spring Harbor Laboratory; (1988).

As used herein, the term "purified" or "to purify" refers to the removal of contaminants from a sample. For example, effector (non-memory) T cells that are potentially reactive with a host may be deleted by removal of such cells based on cell surface phenotype. The removal of undesirable cells results in an increase in the percentage of desired cells in the sample As used herein, the terms "treat," "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

Cancer is "inhibited" if at least one symptom of the cancer is alleviated, terminated, slowed, or prevented. As used herein, cancer is also "inhibited" if recurrence or metastasis of the cancer is reduced, slowed, delayed, or prevented. Similarly, a person with cancer is "responsive" to a treatment if at least one symptom of the cancer is alleviated, terminated, slowed, or prevented. As used herein, a person with cancer is also "responsive" to a treatment if recurrence or metastasis of the cancer is reduced, slowed, delayed or prevented.

Memory T Cell. A number of phenotypically distinct memory T cells have been described in the art and phenotypically characterized. Memory T cells of interest for the present methods are generally CD8+ cells, which may include one or both, usually both, of central and effector memory cells. Central memory T cells have been described as L-selectin and CCR7 positive, as well as secreting IL-2, but not IFNγ or IL-4. Effector memory T cells, are reported to lack expression of L-selectin or CCR7 but produce effector cytokines including IFNγ and IL-4.

Such cells may be isolated from donor peripheral blood mononuclear cells, and are typically selected for expression of CD8. The cells are optionally selected as being one or more of CD44 positive in mice; CD56 negative, CD57 negative, and may be subdivided by expression of CD45 markers in humans, for example CD45RO$^+$ CD45RA$^-$. See, for example, Cui et al. (2010) Immunol Rev. 236:151-66; Lefrançois et al. (2010) Immunol Rev. 235(1):206-18; Zanetti et al. (2010) Adv Exp Med Biol. 684:108-25; Suzuki et al. (2008) Hum Immunol. 69(11):751-4; Tough (2003) Trends Immunol. 24(8):404-7; each herein specifically incorporated by reference.

Memory T cells may be obtained from a suitable source, including human peripheral blood, bone marrow, lymph node, umbilical cord, in vitro cell cultures and the like. Such samples can be separated by centrifugation, elutriation, density gradient separation, apheresis, affinity selection, panning, FACS, centrifugation with Hypaque, etc. prior to analysis, and usually a mononuclear fraction (PBMC) will be used. Once a sample is obtained, it can be used directly, frozen, or maintained in appropriate culture medium for short periods of time. Various media can be employed to maintain cells. The samples may be obtained by any convenient procedure, such as the drawing of blood, apheresis, venipuncture, biopsy, or the like. An appropriate solution may be used for dispersion or suspension of the cell sample. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

Cell staining and selection for enrichment of the desired memory T cell population will use conventional methods. Techniques providing accurate selection include fluorescence activated cell sorters, magnetic selection methods, affinity columns and the like.

The affinity reagents may be specific receptors or ligands for the cell surface molecules indicated above. Of particular interest is the use of antibodies as affinity reagents. Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The antibodies are added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium that maintains the viability of the cells. A preferred medium is phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc.

The cells are selected for the expression of cell surface markers as previously described. Usually the cells to be provided to a patient will be at least about 50% of the selected phenotype, at least about 70%, at least about 80%, at least about 90%, at least 95% or more of the desired phenotype.

The cells are administered in an effective dose to provide for substantially complete chimerism of the recipient hematopoietic system to the donor cell genotype. Additionally, the dose may be sufficient to inhibit or kill tumor cells, where such cells are present. As an example, for an adult human the cell dose may be at least about $10^6$ cells, at least about $10^7$ cells, at least about $10^8$ cells, or more. For pediatric patients the dose may be reduced appropriately, e.g. at least about $5\times10^5$, at least about $10^6$, at least about $10^7$ or more cells.

The cells are administered to a patient following allogeneic hematopoietic cell transplantation (HCT), where such transplantation may be utilized for treatment of cancer or for other conditions requiring reconstitution of the hematopoietic system, e.g. treatment of anemias, thalassemias, autoimmune conditions, and the like, at a suitable time following transplantation in humans, e.g., from about 2 to about 6 months to prevent relapse or at the time of relapse to treat relapse.

In one embodiment of the invention, compositions and methods are provided for augmenting the treatment of cancer, including without limitation leukemias and lymphomas, after allogeneic hematopoietic cell transplantation by adding a purified subset of donor lymphocytes that can kill the tumor cells without inducing the major complication of graft versus host disease (GVHD).

In a related embodiment, methods and compositions are provided to augment the conversion of mixed hematopoietic cell chimerism to complete donor cell chimerism following allogeneic hematopoietic cell transplantation (HCT), where such transplantation may be utilized for treatment of cancer or for other conditions requiring reconstitution of the hematopoietic system, e.g. treatment of anemias, thalassemias, autoimmune conditions, and the like. Mixed chimerism is associated with a much higher rate of cancer progression or relapse compared to patients who achieve full donor chimerism by following allogeneic HCT. Although donor lymphocyte infusions (DLI) may be conventionally given at a time point after transplantation, DLI is ordinarily made up of peripheral blood mononuclear cells that contain all subsets of T cells in the blood and thus carries a major risk of inducing severe GVHD.

In some embodiments, the present invention provides a method of treating cancer comprising treating a patient with a chemotherapeutic or radiological agent; substantially ablating the recipient hematopoietic system; performing allogeneic transplantation of the hematopoietic cells, including stem cells, and following the transplantation, infusing into the patient a population of donor-derived memory CD8+ T cells, as described above. Examples of cancer that can be treated by the subject methods of the present invention include but are not limited to lymphomas, leukemias, and solid tumors such as colorectal cancer, lung cancer, pancreatic cancer, breast cancer, prostate cancer, liver cancer, and ovarian cancer. The tumor can be primary or metastatic.

In studies in mice, T cell depleted bone marrow transplants were given to recipients with a B cell lymphoma after conditioning with total body irradiation. The recipients became mixed chimeras and the tumor grew progressively. The recipients were given a DLI after about 2-3 weeks that was either made up of total T cells or memory CD8+ T cells (CD8+CD44hi) purified by flow cytometry. Whereas the total T cell DLI induced lethal GVHD, the memory CD8+ DLI eradicated the tumor without causing GVHD. The CD8+ T cells also facilitated the conversion to complete donor chimerism. The mouse memory CD8+ T cells responded to alloantigens in vitro by proliferation and IFN-gamma secretion with little IL-2 secretion. Similarly, human memory CD8+ T cells (CD8+CD45RO+) responded to alloantigens in vitro with proliferation and IFN gamma secretion with little IL-2 secretion.

Combined $CD8^+$ central and effector memory ($CD8^+ CD44^{hi}$) T cells freshly isolated from unprimed donors, or effector memory $CD8^+$ T cells generated after culturing donor $CD8^+$ T cells with host type dendritic cells, failed to induce GVHD in previous studies of MHC-matched mice.

Bone marrow transplantation has become well established in the treatment of malignant disorders. High-dose chemotherapy with hematopoietic stem cell support is widely used for most hematological malignancies, as well as for some solid tumors. In light of recent developments in blood progenitor cell harvest, in particular, the availability of large numbers of blood stem cells, mobilized by granulocyte colony-stimulating factor and collected by leukapheresis, it is possible to overcome histocompatibility barriers in HLA-mismatched patients. Other recent developments including but not limited to new methods for blood progenitor cells mobilization and ex vivo expansion of progenitor cells and immune cells, the use of umbilical cord blood as an alternative source of stem cells, and other molecular techniques, support an effective treatment of cancer via allogeneic transplantation of hematopoietic and immune cells.

Clinical Efficacy

Tumor growth and disease progression is monitored during and after treatment of cancer via the subject methods of the present invention. Clinical efficacy can be measured by any method known in the art. In some embodiments, clinical efficacy of the subject treatment method is determined by measuring the clinical benefit rate (CBR).

The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD months. In some embodiments, CBR for the subject treatment method is at least about 50%. In some embodiments, CBR for the subject treatment method is at least about 55%, 60%, 65%, 70%, 75%, 80%, 85%, 90%, 95% or more.

In the present invention, the preclinical data show improved tumor killing and reduced graft v host disease by treating tumor bearing hosts with allogeneic hematopoietic cell transplantation following by infusion of donor derived CD8+ memory T cells.

An important limitation of allogeneic HCT is the development of graft versus host disease (GVHD), which occurs in a severe form in about 30-50% of humans who receive this therapy. GVHD is substantially reduced by performing a memory T cell infusion using the methods of the invention.

The term "subject" as used herein includes humans as well as other mammals. The term "treating" as used herein includes achieving a therapeutic benefit and/or a prophylactic benefit. By therapeutic benefit is meant eradication or amelioration of the cancer. Also, a therapeutic benefit is achieved with the eradication or amelioration of one or more of the physiological symptoms associated with cancer such that an improvement is observed in the animal subject, notwithstanding the fact that the animal subject may still be afflicted with that cancer.

The types of cancer that can be treated using the subject methods of the present invention include but are not limited to leukemia, lymphoma, adrenal cortical cancer, anal cancer, aplastic anemia, bile duct cancer, bladder cancer, bone cancer, bone metastasis, brain cancers, central nervous system (CNS) cancers, peripheral nervous system (PNS) cancers, breast cancer, cervical cancer, childhood Non-Hodgkin's lymphoma, colon and rectum cancer, endometrial cancer, esophagus cancer, Ewing's family of tumors (e.g. Ewing's sarcoma), eye cancer, gallbladder cancer, gastrointestinal carcinoid tumors, gastrointestinal stromal tumors, gestational trophoblastic disease, hairy cell leukemia, Hodgkin's lymphoma, Kaposi's sarcoma, kidney cancer, laryngeal and pharyngeal cancer, acute lymphocytic leukemia, acute myeloid leukemia, children's leukemia, chronic lymphocytic leukemia, chronic myeloid leukemia, liver cancer, lung cancer, lung carcinoid tumors, male breast cancer, malignant mesothelioma, multiple myeloma, myelodysplastic syndrome, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcomas, melanoma skin cancer, non-melanoma skin cancers, stomach cancer, testicular cancer; thymus cancer, thyroid cancer, uterine cancer (e.g. uterine sarcoma), transitional cell carcinoma, vaginal cancer, vulvar cancer, mesothelioma, squamous cell or epidermoid carcinoma, bronchial adenoma, choriocarinoma, head and neck cancers, teratocarcinoma, or Waldenstrom's macroglobulinemia.

In some embodiments, the subject method further comprises administering to a subject in need thereof an anti-tumor agent, or a pharmaceutically acceptable salt or prodrug thereof. In some embodiments, the anti-tumor agents include but are not limited to antitumor alkylating agents, antitumor antimetabolites, antitumor antibiotics, plant-derived antitumor agents, antitumor organoplatinum compounds, antitumor campthotecin derivatives, antitumor tyrosine kinase inhibitors, monoclonal antibodies, interferons, biological response modifiers, and other agents having anti-tumor activities, or a pharmaceutically acceptable salt thereof.

EXPERIMENTAL

Example 1

$CD8^+$ $CD44^{hi}$ but not $CD4^+$ $CD44^{hi}$ Memory T Cells Mediate Potent Graft Anti-Lymphoma Activity without GVHD Freshly isolated naive $CD4^+$, $CD8^+$ or total T cells, and/or memory $CD4^+$ $CD44^{hi}$, $CD8^+$ $CD44^{hi}$, and total T $CD44^{hi}$ cells from unprimed donors were compared for their capacity to induce GVHD, promote complete chimerism, and mediate anti-tumor activity against a naturally occurring B cell lymphoma ($BCL_1$) in an MHC-mismatched model. Only the $CD8^+$ $CD44^{hi}$ memory T cell subset containing both central and effector memory cells was capable of eradicating the lymphoma cells without inducing GVHD. In contrast, $CD4^+$ and $CD8^+$ naive T cells, memory $CD44^{hi}$ $CD4^+$ T cells, naive total T cells, and memory total T $CD44^{hi}$ cells either induced lethal GVHD or lacked potent anti-tumor activity. The tumor bearing recipients of $CD8^+$ $CD44^{hi}$ T cells had a clear survival advantage over those given $CD8^+$ naive T cells due to the lethal GVHD induced by the latter cells. The $CD8^+$ $CD44^{hi}$ T cells were also used in a model of treatment of progressive lymphoma growth after bone marrow transplantation, and were able to promote complete chimerism, and eradicate the tumor without GVHD.

Materials and Methods

Animals. Wild type Thy1.2 C57BL/6 ($H-2^b$) male mice, 8 to 12 weeks old and male BALB/c ($H-2^d$) Thy 1.2 mice 8 to 12 weeks old were purchased from the breeding facility of the Department of Comparative Medicine, Stanford University or The Jackson Laboratory (Bar Harbor, Me., USA). The luciferase-expressing ($luc^+$) transgenic B6-L2G85 ($H-2^b$, Thy1.1) mice were utilized as described previously[16]. All mice were housed in a specific pathogen free facility. Care of all experimental animals was in accordance with institutional and National Institutes of Health guidelines.

Antibodies and Flow Cytometric Analysis (FACS). Unconjugated anti-CD16/32 (2.4G2), anti-CD8 PE (53-6.7), anti-TCRβ APC (H57-597), anti-CD62L FITC (Mel-14), anti-CD44 PE (IM7), anti-LPAM-1 PE ($α_4β_7$ integrin complex) (DATK32), anti-$H-2K^b$ FITC (AF6-88.5), anti-CD19 APC (1D3), anti-B220 Pacific Blue (RA36B2) monoclonal antibodies (mAbs) were purchased from BD Pharmingen (San Diego, Calif.). Anti-CD8 Alexa 700 (53-6.7) and anti-Thy1.1 Pacific Blue (OX-7) were obtained from Biolegend (San Diego, Calif.). Anti-CCR9 PE (242503) and anti-CXCR3 PE (220803) mAbs were purchased from R&D systems (Minneapolis, Minn.). Anti-idiotype $BCL_1$ antibody was purified from a hybridoma secreting rat IgG2a. The antibody was conjugated with Alexa-Fluor-488 for FACS staining. Staining and flow cytometric analysis and sorting have been described in detail previously.

Cell Preparations. Single spleen cell suspensions were enriched for $CD4^+$, $CD8^+$ or TCR $β^+$ total T cells with anti-CD4 and anti-CD8 magnetic microbeads using the MidiMACS® system (Miltenyi Biotech, Auburn, Calif.). After staining with anti-CD8 PE, anti-CD4, anti-CD62L FITC and anti-CD44 APC, cells were sorted into $CD62L^{hi}CD44^{lo}$ naive or total $CD44^{hi}$ (memory) populations using an Aria flow cytometer (Becton-Dickinson, Mountain View, Calif.). The sorted naive and memory cells were ≥98% pure as judged by re-analysis of sorted cells. Preparation of T cell-depleted bone marrow (TCD BM) cells, has been reported before. To monitor $BCL_1$ tumor cells and donor chimerism in peripheral blood of transplanted mice, red cells were lysed and enriched white blood cells were used for FACS staining.

Mixed Leukocyte Reaction, Cytokine Assay, and Cytotoxicity Assay. Sorted naive or memory $CD8^+$ T cell subsets from C57BL/6 donor mice were used as responders and mixed with irradiated (3,000 cGy) allogeneic BALB/c splenocytes as stimulators in the mixed leukocyte reaction (MLR) as described. $^3$[H]thymidine incorporation was measured after 5 days, and cytokine secretion in supernatants was analyzed in a multiplex assay system with microsphere beads after 60 hours. Sorted naive or memory phenotype $CD8^+$ T cells were stimulated in a 1:2 ratio with irradiated (3,000 rads) BALB/c splenocytes for 96 hours. Cultured cells were used as effector cells, and mixed with luciferase expressing $BCL_1$ luc/gfp lymphoma target cells. Cytolysis was assessed by bioluminescence imaging as described before.

GVHD Model, Histopathological Scoring for GVHD Severity, and $BCL_1$ Tumor Model. Acute GVHD was induced as described previously. In brief, BALB/c hosts were given 800 cGy of total body irradiation from a 200 Kv X-ray source, and injected with donor cells via the tail vein within 24 hours. Histologic assessment of liver, small bowel and colonic GVHD was performed in a blinded fashion using the histopathologic scoring system described by Kaplan et al. $BCL_1$ is a spontaneously arising B-cell leukemia/lymphoma derived from BALB/c mice with an IgMλ surface Ig phenotype. This cell line was maintained by serial passage in BALB/c mice as described previously. The use of $BCL_1$ tumor cells with the luc-gfp gene construct has been reported before.

In Vivo and Ex Vivo Bioluminescence Imaging. In vivo bioluminescence imaging was performed according to Edinger et al. Briefly, mice were injected intraperitoneally with luciferin (10 μg/g body weight). Ten minutes later, mice were imaged using an IVIS100 charge-coupled device imaging system (Xenogen, Alameda, Calif.) for 5 minutes. Imaging data were analyzed and quantified with Living Image Software (Xenogen). Ex vivo bioluminescence imaging was performed according to the method described by Beilhack et al.

In vivo CFSE proliferation assay. For analysis of cell proliferation, sorted naive or memory $CD8^+$ T cells from Thy1.1 C57BL/6 donors were loaded with a Vybrant CDDA SE (carboxyfluorescein diacetate, succinimidylester) Tracer kit (Invitrogen, Carlsbad, Calif.) as described. Thy1.1 CFSE labeled naive and memory cells ($0.5×10^6$) along with $2×10^6$ TCD BM cells (C57BL/6, Thy1.2) were injected into lethally irradiated BALB/c mice. On day 3+ after BMT, the CFSE staining of the infused Thy1.1 cells from the spleen were analyzed by FACS, and comparisons of the number of cell divisions were made using proliferation analysis with Flowjo software.

Statistical Analysis. Kaplan-Meier survival curves were made using Prism (GraphPad Software, San Diego, Calif.). Statistical differences in animal survival were analyzed by log-rank test. Differences in mean $^3$[H]thymidine incorporation and cytokine production of replicate in vitro assays were analyzed using the two-tailed Student t test. Mann-Whiltney U test was used for comparison of GVHD scores. For all tests, $p≤0.05$ was considered significant.

Results

GVHD and Anti-Lymphoma Activity of Donor T Subsets. We searched for freshly isolated donor T cells that had graft anti-lymphoma activity without inducing severe GVHD. Initially, lethally irradiated BALB/c ($H-2^d$) hosts were transplanted with $2×10^6$ C57BL/6 ($H-2^b$) donor TCD BM cells along with a constant number ($0.5×10^6$) of total T cells (naive and memory unseparated) or $CD4^+$ T cells (naive and memory unseparated). Hosts transplanted with TCD BM alone survived over 100 days and their weights returned to pre-transplant levels (FIG. 1A). The $CD4^+$ and total T cells added to TCD BM induced acute GVHD within a week of transplantation, leading to diarrhea, progressive weight loss and death of all recipients by three weeks of transplant (FIG. 1). Body weight and survival were significantly reduced as compared to that of recipients given TCD BM alone (p≤0.0001 and p<0.001 respectively) (FIGS. 1A and B).

Several previous studies including ours have shown that $CD44^{hi}$ memory $CD4^+$ T cells do not induce lethal GVHD[10]. We determined the survival and appearance of tumor cells in the blood of BALB/c transplant recipients given C57BL/6 $CD44^{hi}$ memory $CD4^+$ T cells, TCD BM and $BCL_1$ lymphoma cells. Other groups received naive $CD4^+$ T cells, naive total T cells or memory total T cells instead of memory $CD4^+$ T cells at the same dose (FIGS. 1C-F). All animals that received TCD BM alone died, and developed lymphoma cells in the blood by day 28 (FIG. 1D). There were no signs of GVHD. The animals that received naive $CD4^+$ T or naive total T cells along with TCD BM succumbed to lethal GVHD with severe diarrhea and weight loss within 10 days of transplantation (FIGS. 1C and E). Although the recipients of memory $CD4^+$ T cells and TCD BM did not show signs of GVHD, they were unable to control the lymphoma growth and all died within 30 days of transplantation with $BCL_1$ idiotype positive cells in peripheral blood (FIG. 1D). Interestingly, 40% of the hosts that received memory total T cells died with lymphoma cells in the blood, (FIG. 1F). The remaining 60% of the hosts did not develop lymphoma cells in blood, and survived over 100 days without clinical signs of GVHD (FIG. 1E).

Figure 2:
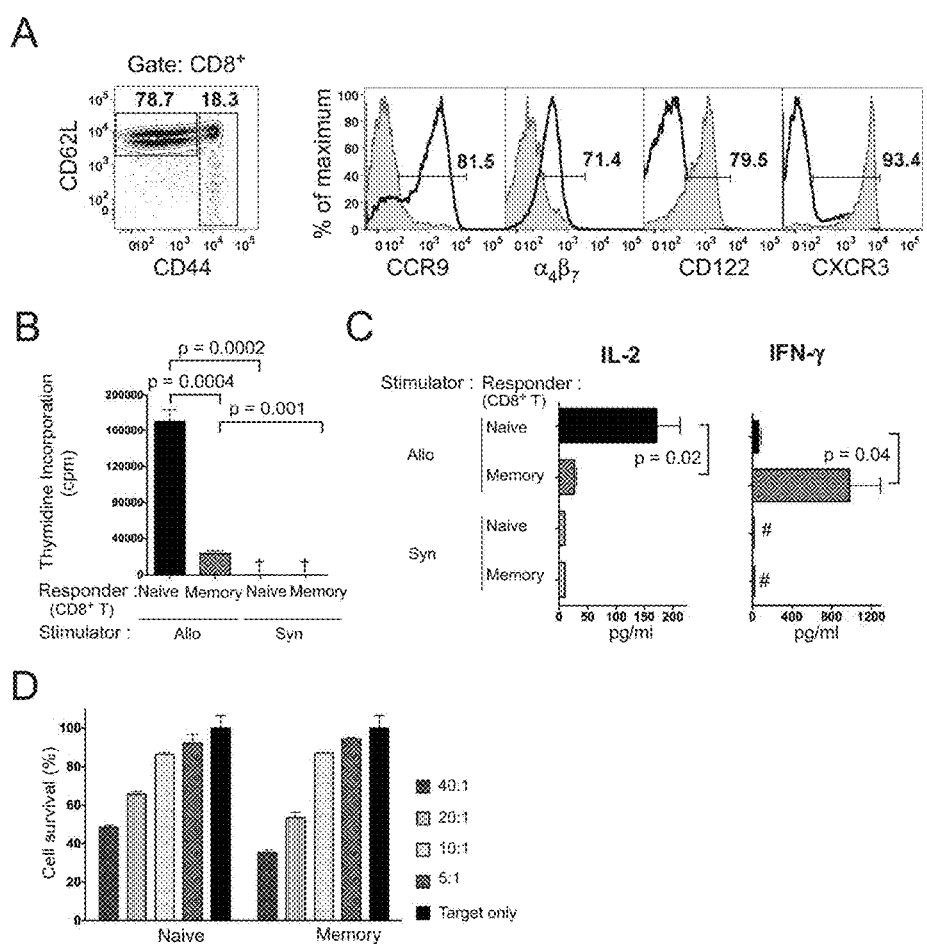
FIG. 2. Characterization of Naive and Memory Phenotype $CD8^+$ T cells. A, C57BL/6 splenocytes were stained with anti-CD8, anti-CD44, and anti-CD62L mAbs. Gated $CD62L^{hi}CD44^{low}$ and $CD44^{hi}$ $CD8^+$ T were analyzed for CCR9, $a_4\beta_7$, CD122, and CXCR3 expression. Gates were determined by isotype staining. Histogram plots of the respective markers are overlaid for $CD44^{lo}$ $CD8^+$ T cells (bold line) and $CD44^{hi}$ $CD8^+$ T (tinted area). B, $^3$H-thymidine incorporation (mean±SE) of C57BL/6 responder naive or memory phenotype $CD8^+$ T cells ($2\times10^5$) to BALB/c stimulator cells ($8\times10^5$) at day 5 in the MLR in three replicate wells for each cell combination. Results are representative of at least 3 MLR experiments. Allo and Syn denote BALB/c and C57BL/6 stimulator cells, respectively. † indicates that $^3$H-thymidine incorporation was less than 5,000 cpm C, Cytokine responses of C57BL/6 donor naive or memory phenotype $CD8^+$ T cells ($1\times10^5$) to irradiated BALB/c stimulator cells ($5\times10^5$) in the MLR are shown at 60 h. Left panel shows the mean±SEM concentrations of IL-2; Right shows the mean±SEM concentrations of IFN-γ. #, The concentration of cytokine was <10 pg/ml. Results are representative of at least three MLR cultures. D, Sorted Naive and memory cells were used in a cytotoxicity assay against Luciferase expressing—$BCL_1$ cells. Sorted Naive or memory phenotype $CD8^+$ T cells were stimulated with irradiated BALB/c splenocytes for 96 hours. $BCL_1$ lymphoma cells expressing luciferase were mixed with stimulated naive or memory phenotype cells at various effector: target ratios. Luciferase signal was measured after 16 hours. Percent cytotoxicity was then determined as compared with the same target numbers without effector cells at each time point.

$CD8^+$ Naive and Memory T Cells from Unimmunized Donors are Alloreactive. We went on to study separated naive and memory $CD8^+$ T cell for alloreactivity in vitro, and for GVHD and GVT activity. Initially, we analyzed the gated naive $CD8^+$ T and memory $CD44^{hi}$ $CD8^+$ T cells from untreated C57BL/6 mice for expression of CCR9, $\alpha_4\beta_7$, CXCR3 and CD122. Naive $CD8^+$ T cells showed intense staining for CCR9 and dull staining for $\alpha_4\beta_7$ while memory $CD8^+$ T cells showed negative staining for both (FIG. 2A). The memory phenotype cells displayed higher levels of CXCR3 and CD122 than naive cells (FIG. 2A) confirming that these are memory markers as described before.

In order to assess the alloreactivity of the cell subsets, sorted naive or memory C57BL/6 $CD8^+$ T cells were incubated with irradiated BALB/c spleen cells as allogeneic stimulators. A constant number of sorted responder cells ($1\times10^5$) were incubated with a constant number of stimulator cells ($4\times10^5$). The proliferation was measured after 5 days in culture, and IL-2 and IFN-γ cytokine secretion was measured in the supernatants after 60 h in culture. Our previous studies using this culture system showed that naive $CD4^+$ T cells were alloreactive, but that memory $CD4^+$ T cells were not as judged by proliferation and cytokine secretion that were no greater than background. The naive $CD8^+$ T cells incorporated 7 fold more $^3$H thymidine than the memory $CD8^+$ T cells (p=0.0004) (FIG. 2B). Both subsets incorporated significantly more $^3$H-thymidine with allogeneic stimulators as compared to syngeneic. FIG. 2C shows that sorted naive $CD8^+$ T cells secreted mean concentrations of IL-2 that were 150-200 pg/ml after culture with allogeneic stimulators, and differences between the allogeneic and syngeneic cultures were significant (p<0.01). In contrast, the mean concentration of IL-2 secreted by sorted memory $CD8^+$ T cells was below 50 pg/ml in both allogeneic and syngeneic cultures (p=0.02 memory vs naive for allo) (FIG. 2C). FIG. 2C shows that allogeneic cultures with sorted memory cells $CD8^+$ T cells secreted IFN-γ (mean about 1000 pg/ml) that was significantly increased as compared to allogeneic cultures with naive $CD8^+$ T cells (p=0.04) or to syngeneic cultures (p<0.005). All cultures were assayed for IL-4, IL-10 and TNFα in the supernatants, however these cytokines were not detected in multiplex cytokine assays.

To investigate the cell mediated cytotoxicity of the memory and naive phenotype $CD8^+$ T cells, we used $BCL_1$ lymphoma target cells transduced with the luciferase gene construct. The naive and memory $CD8^+$ T were activated in allogeneic cultures with irradiated BALB/c stimulator cells for 96 hours. These activated cells were used as effector cells in different ratios against $BCL_1$ target cells. The enzymatic activity of luciferase was used as a measure of $BCL_1$ cell survival. The percentage of $BCL_1$ cell cytolysis was similar with naive and memory $CD8^+$ T cells in all cell ratios tested (FIG. 2D). Therefore both the subsets displayed similar ability to kill the tumor cells.

Figure 3:
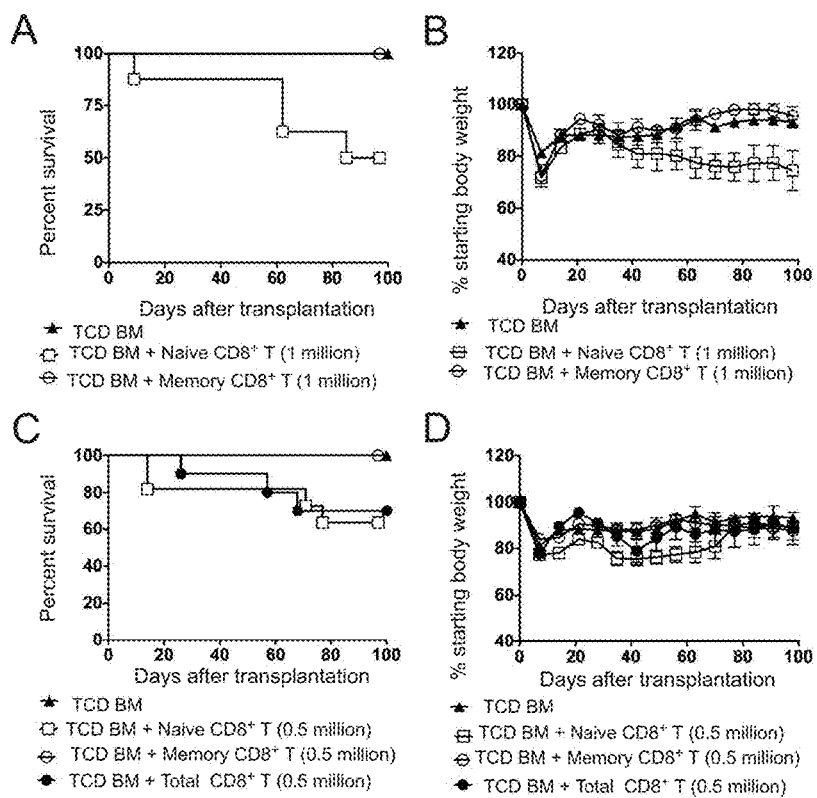
FIG. 3. Survival and weight changes of BALB/c recipients transplanted with donor C57BL/6 TCD BM cells with or without sorted, total, naive, or memory phenotype $CD8^+$ T cells. A and C, Survival of lethally irradiated BALB/c hosts given $2\times10^6$ TCD BM cells from donors with or without $1.0\times10^6$ naive, $1.0\times10^6$ memory, $0.5\times10^6$ naive, $0.5\times10^6$ memory, or $0.5\times10^6$ total $CD8^+$ donor T cells (N=8-11) is shown. The data were pooled from two independent experiments. B and D, Percentage of starting body weight of host mice given TCD BM with or without sorted naive, memory, or total $CD8^+$ T cells as in A and C. Brackets show SEs of the mean.

$CD8^+$ Naive but not Memory T Cells Induce Lethal GVHD. In further experiments, irradiated BALB/c hosts received either $1.0\times10^6$ or $0.5\times10^6$ doses of naive or memory C57BL/6 donor $CD8^+$ T cells and/or $2\times10^6$ TCD BM cells. FIGS. 3A and 3C show that all irradiated recipients that received only TCD BM cells survived for 100 days. Although there was a transient weight loss during the first week after irradiation, there was a recovery to baseline during the third week and stabilization thereafter (FIG. 3B). These mice did not show typical clinical features of GVHD including diarrhea, hunched back, ruffled fur, hair loss, and facial swelling. In contrast, about 50% of the hosts that received $1\times10^6$ naive $CD8^+$ T cells developed diarrhea around day 40, and showed progressive weight loss until death between 60-100 days after transplantation (FIGS. 3A and B). In contrast, all recipients survived in the memory $CD8^+$ T cell group (FIG. 3A). There were significant differences in survival (p<0.05) and weight loss (p<0.01) between naive and memory $CD8^+$T cell groups. When the hosts received a lower cell dose of $0.5\times10^6$ naive $CD8^+$ T cells, about 40% succumbed with clinical features of GVHD (FIG. 3C). The survival of recipients given $0.5\times10^6$ total $CD8^+$ T cells was similar to that of recipients given the same dose of naive $CD8^+$ T cells. Both the total $CD8^+$ T cells and naive $CD8^+$ T cells significantly reduced survival as compared to that of memory $CD8^+$ T cells (p=0.04), (FIG. 3C). Autopsies showed histopathologic evidence of GVHD (data not shown). All the recipients of memory phenotype $CD8^+$ T cells at this cell dose survived over 100 days and showed similar weight loss as the TCD BM group (FIG. 3D). The difference between the survival and weight loss in naive and memory group was significant (p<0.05) (FIG. 3D).

Figure 4:
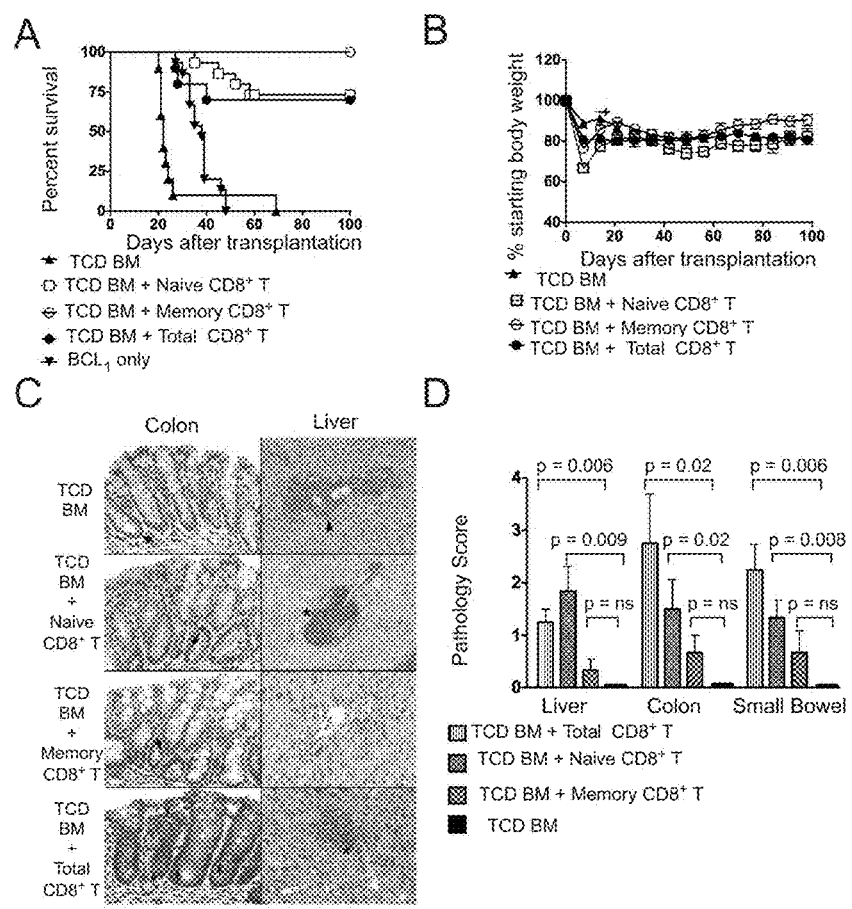
FIG. 4. Survival, weight changes and organ pathology scores of BALB/c hosts that received 500 $BCL_1$ lymphoma cells followed by transplantation of TCD BM from C57BL/6 donors with or without sorted naive, or memory, or total $CD8^+$ T cells. The hosts received 500 $BCL_1$ lymphoma cells 6 hours after irradiation. A, Survival of irradiated hosts given $2\times10^6$ TCD BM cells from C57BL/6 donors with or without (N=10) $0.5\times10^6$ sorted naive (N=14), memory (N=12), or total $CD8^+$ T cells (N=10). The data were pooled from 2-4 independent experiments. B, Percentage of starting body weight of host mice given TCD BM with or without sorted naive, memory, or total $CD8^+$ T cells as in A. Brackets show SEs of the mean. C, Histopathologic changes induced with naive, memory phenotype, or total $CD8^+$ T cells and TCD BM only. Representative tissue sections were obtained from hosts in A. Histopathological specimens from the liver and large intestines of hosts were obtained at 100 days after transplantation and fixed in formalin before embedding into paraffin blocks. Tissue sections of 4-5 mm thickness were stained with hematoxylin and eosin. Microscopic images were obtained using an Eclipse E1000M microscope (Nikon, Melville, N.Y.) with SPOT RT digital camera and acquisition software (Diagnostic Instruments, Sterling Heights, Mich.) with a final magnification of 300× for all images. Image processing was performed with Photoshop CS (Adobe, San Jose, Calif.) with standard adjustments of brightness, contrast and color balance to the entire image. Histopathology at day 21 in the TCD BM group (upper photos). Except for rare apoptosis (arrow, left photo), there was no evidence of GVHD in the colon, but lymphoma was evident (arrowhead, right photo) in liver. In naive group (second row photos), there is no evidence of GVHD in colon. Liver portal tracts have prominent lymphocytic infiltrates compatible with grade 2 GVHD (asterix, right photo). In memory group (third row photos), there is no evidence of GVHD or lymphoma in either colon or liver. In TCD BM with total $CD8^+$ T cell group, increased apoptosis was seen in colonic crypts (arrow) along with increased lamina propria inflammation (open arrowhead, left photo, fourth row). Similarly, portal inflammation and bile duct injury (asterix) was seen in liver compatible with GVHD. Tissue sections were stained with H&E. Each photo is representative of 5-10 hosts examined. D, Mean (±SE) of histopathologic GVHD scores of liver, small bowel, and colon from the four groups (N=6 per group). NS=not significant p>0.05)
Figure 5:
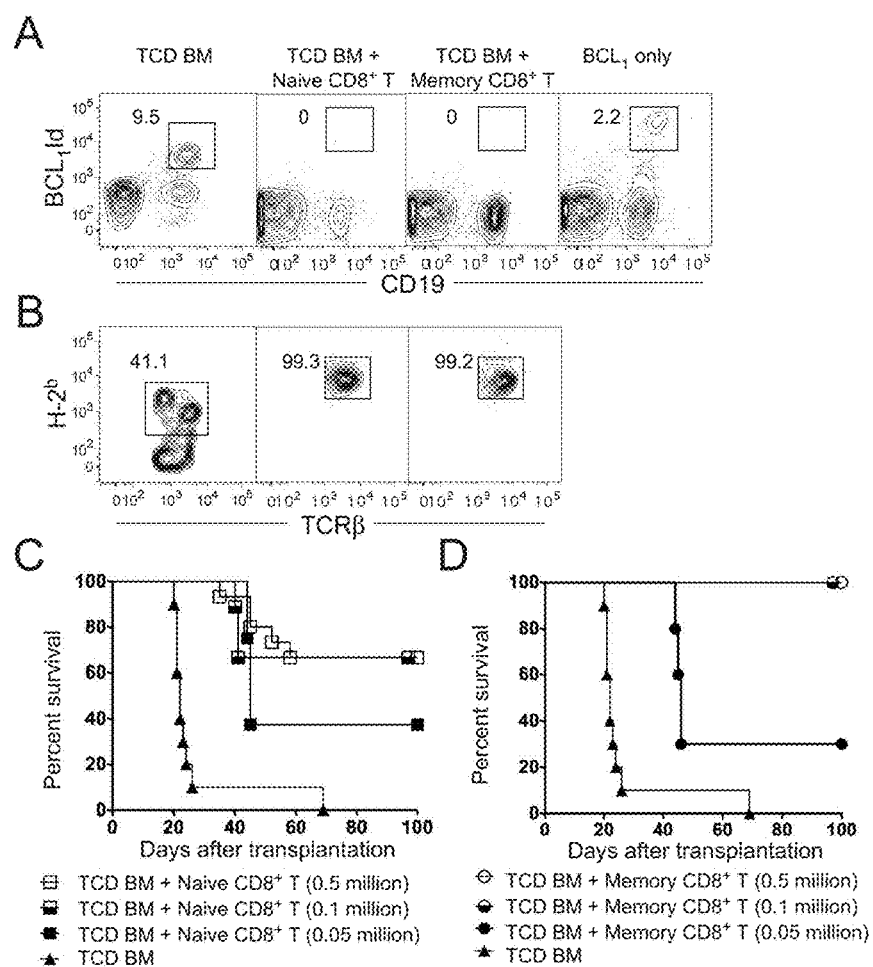
FIG. 5. Survival, chimerism, and elimination of $BCL_1$ tumor cells after transplantation of TCD BM with or without sorted naive or memory $CD8^+$ T cells. A, Representative two-color flow cytometric analysis of CD19 versus $BCL_1$-idiotype markers in the peripheral blood from recipients 28 days after total body irradiation (TBI, 800 cGy), $BCL_1$ cells, and a transplant of $2\times10^6$ TCD BM marrow cells with or without 0.5 million naive or memory phenotype $CD8^+$ T cells. Untreated control recipients were given $BCL_1$ only. The boxes enclose $BCL_1$ idiotype$^+$ $CD19^+$ cells, and percentages of cells in boxes are shown. B, Representative flow cytometric analysis of peripheral blood at day 28 showing percentage of donor (H-$2K^{b+}$) cells among gated $TCR\beta^+$ cells. C and D, Survival of lethally irradiated BALB/c hosts given $2\times10^6$ TCD BM cells from C57BL/6 donors with or without (N=8) $0.5\times10^6$, $0.1\times10^6$ or $0.05\times10^6$ sorted naive (N=15; N=9; N=8) (C) or memory phenotype phenotype (D) $CD8^+$ T cells (N=12; N=9; N=8). The data were pooled from two independent experiments.

$CD8^+$ Memory T Cells Mediate Anti-Lymphoma Activity with Minimal GVHD. We assessed the anti-tumor activity of donor cells in lethally irradiated BALB/c mice that were given 500 $BCL_1$ lymphoma cells (non transduced) followed by $2\times10^6$ TCD BM with or without $0.5\times10^6$ total $CD8^+$ T cells or sorted naive or memory $CD8^+$ T cells. Most of the mice that received TCD BM only died by day 30 after transplantation (FIG. 4A) associated with the presence of $BCL_1$-idiotype$^+$ tumor cells in the blood (FIG. 5A). Survival of hosts was significantly improved in the groups that received total $CD8^+$ T (p<0.0001), naive $CD8^+$ T cells (p<0.0001) or memory $CD8^+$ T cells (p<0.0001) compared to the hosts that received TCD BM only (FIG. 4A). About 25% of hosts died by day 60 in the total $CD8^+$ T cell and naive $CD8^+$ T cell groups, and all hosts in this group had no detectable tumor cells in the blood (FIGS. 4A and 5A). All the mice that received memory $CD8^+$ T cells survived over 100 days without any tumor cells in blood (FIGS. 4A and 5A). The survival was significantly decreased between groups given total $CD8^+$ T cells or naive $CD8^+$ T cells, as compared to the group given memory CD8+ T cells (p=0.03 and p=0.04 respectively). Weight loss was also significantly different (p=0.03 and p=0.004). All untreated mice that received BCL$_1$ tumor cells died by day 50.

FIG. 4C shows representative tissue sections of the colon and the liver of the bone marrow transplant recipients. Whereas the colon of recipients given TCD BM with or without memory CD8+ T cells showed preservation of crypts and goblet cells with minimal lymphocytic infiltration, the recipients given, naive CD8+ T cells or total CD8+ T cells showed drop out of crypts, loss of goblet cells, and considerable infiltrates. The liver of recipients given TCD BM showed tumor cells surrounding blood vessels whereas recipients of naive or total CD8+ T cells showed periportal lymphocytic infiltration. Recipients of memory CD8+ T cells showed neither of the abnormalities. FIG. 4D shows the histopathology scores for GVHD lesions in liver, colon and small intestine. Whereas there were no significant differences between the scores in recipients given TCD BM with or without memory CD8+ T cells (p>0.05), there was a significantly increased score in the groups given TCD BM with naive CD8+ T cells or total CD8+ T cells versus the group with TCD BM alone (p=0.02-0.008). The GVHD score in the liver was significantly higher (p=0.04) in the naive versus memory group.

We assessed the donor cell chimerism among T cells in peripheral blood of the 3 groups of recipients at day 28 (FIG. 5B). All TCD BM transplanted hosts were mixed chimeras as shown in representative staining with donor type (H-2K$^{b+}$) cells among TCRβ+ T cells (FIG. 5B). All recipients given 0.5×10$^6$ naive or memory CD8+ T cells had more than 99% donor type cells, and maintained stable donor chimerism through day 100 (data not shown). Thus, addition of either naive or memory CD8+ T cells resulted in a change from mixed to complete chimerism. Whereas the mixed chimeras developed tumor cells in the blood, the complete chimeras did not (FIG. 5A).

We determined the survival of hosts given lower doses of naive or memory CD8+ T cells along with TCD BM and BCL$_1$ cells. About 70% of the hosts that received 0.5×10$^6$ or 0.1×10$^6$ naive CD8+ T cells survived over 100 days (FIG. 5C), and were free of the BCL$_1$ lymphoma in blood (data not shown). When the cell dose was 0.05×10$^6$, about 30% of the hosts survived over 100 days without tumor cells, and about 70% died with tumor cells in blood. In contrast 100% of the hosts given 0.5×10$^6$ or 0.1×10$^6$ memory CD8+ T cells were able to survive over 100 days without any evidence of lymphoma in blood, but 80% died with lymphoma when dose was reduced to 0.05×10$^6$ (FIG. 5D). The survival of the group given 0.1×10$^6$ memory CD8+ T was significantly improved (p<0.05) as compared to the group given 0.5×10$^6$ total memory T cells shown in FIG. 1E.

Figure 6:
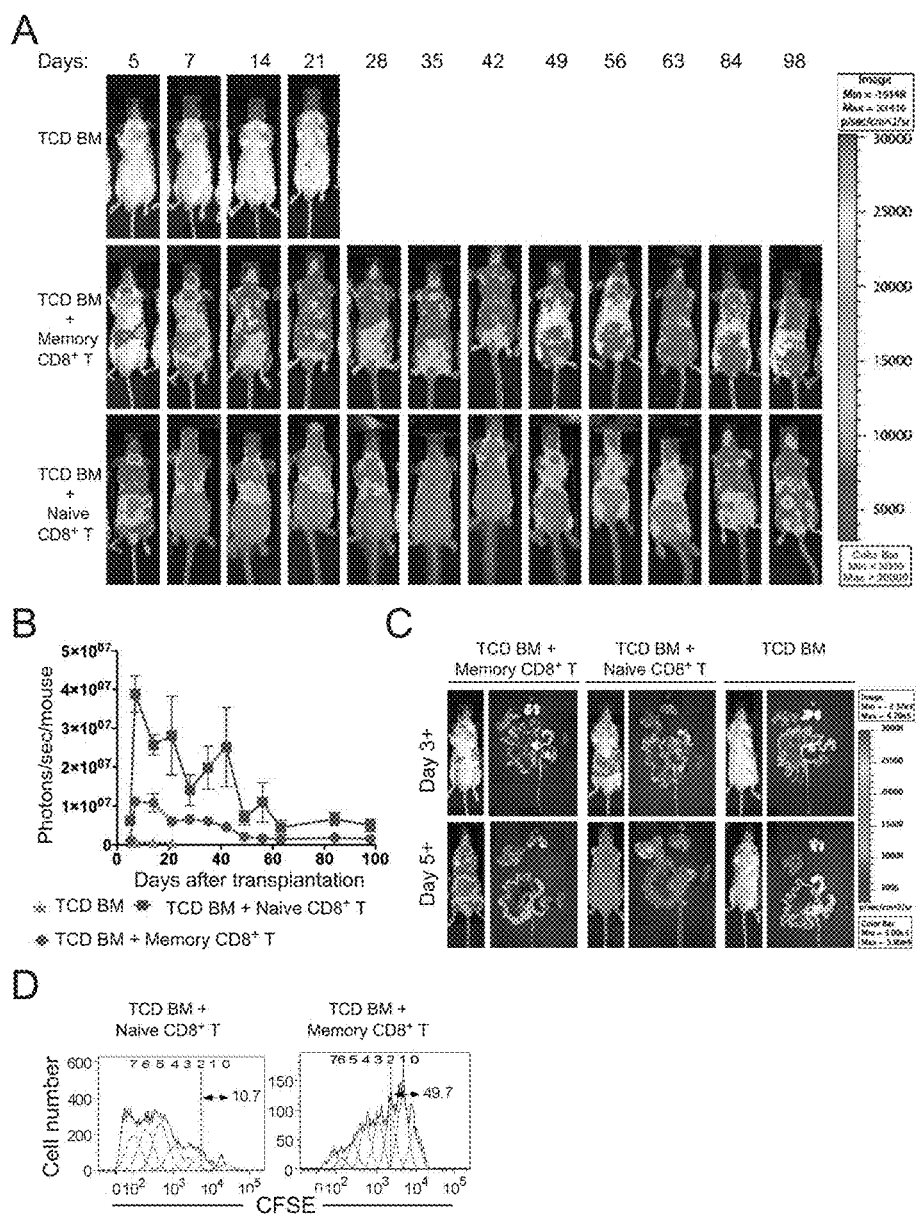
FIG. 6. Comparison of trafficking and proliferation of luciferase transgenic naive and memory $CD8^+$ T cells after transplantation with non-transgenic TCD BM. BALB/c hosts were lethally irradiated, received 500 $BCL_1$ lymphoma cells, and then injected with $2\times10^6$ C57BL/6 (H-$2^b$) wild-type TCD BM cells with $0.5\times10^6$ naive or memory phenotype $CD8^+$ T cells from B6-L2G85 (H-$2^b$)luc+ mice. A, BLI images at serial time points after transplantation. B, Quantitative analysis of photon emission of BLI over time. Recipients in TCD BM group died by day 28. C, In vivo imaging of mice, and ex vivo imaging of intestinal tract (middle position), liver (upper left position), spleen (lower right position) and lungs (upper right position) at day 3+ and day 5+ after transplantation. D, Lethally irradiated BALB/c recipient mice were injected with $2\times10^6$ C57BL/6 (H-$2^b$, Thy1.2) TCD BM cells with either CFSE-labeled $0.5\times10^6$ congenic C57BL/6 (H-$2^b$, Thy1.1) sorted naive or memory phenotype cells $CD8^+$ T cells. On Day 3+, the staining intensity of CFSE from naive and memory phenotype cells Thy1.1+ in the spleen was analyzed. The shaded profile shows staining before transplantation, and the open profile shows staining after.

Rapid Accumulation of CD8+ Naive but not Memory T Cells in the Target Organs of GVHD. In order to account for differences in GVHD severity between naive and memory CD8+ T cells, we investigated whether there are any differences in the extent and rapidity of accumulation of these cells in the lymphoid tissues and in target organs of GVHD. The trafficking and survival of naive and memory CD8+ T cells was evaluated by transplantation of 0.5×10$^6$ naive or memory CD8+ T cells from C57BL/6-L2G85 luc+ mice along with 2×10$^6$ TCD BM from wild type C57BL/6 donors into irradiated BALB/c recipients that received 500 BCL$_1$ tumor cells. Naive CD8+ T cells homed to the spleen and cervical lymph nodes by day 3, and by day 5 intense signals were observed in the gastrointestinal tract and skin (FIG. 6A). The signals were much lower in these organs in mice that received memory CD8+ T cells (FIG. 6A). TCD BM controls had no signal, and these mice died by day 28 due to lymphoma as shown before. The signals from naive CD8+ T cells continued to persist in the gastrointestinal area over the entire observation period of 84 days whereas the signals were lower from memory CD8+ T cells during this period. Quantification of the photon emission by BLI demonstrated that the signals of naive CD8+ T cells increased rapidly up to day 7, and then declined to approach background by day 70 (FIG. 6B). The signal intensity continued to be higher than the memory CD8+ T cells until day 60 (p=0.002) (FIG. 5B). We performed ex vivo BLI imaging on freshly prepared organs such as the liver, spleen, and gastrointestinal tract to analyze the tissue distribution of the signals at days 3+ and 5+ after BMT. Ex vivo images revealed that naive CD8+ T cells homed to secondary lymphoid tissues including the spleen, mesenteric lymph nodes, and Peyer's patches by day 3+, followed by infiltration of the gastrointestinal tract by day 5+(FIG. 6C). The memory CD8+ T cells displayed a similar pattern, however, the signal from the small and large intestines in recipients of memory CD8+ T cells was much weaker and slower than the naive CD8+ T cells (FIG. 6C, day 5).

Increased Cell Division of CD8+ Naive Versus Memory T Cells in the Spleen. The observations from BLI studies prompted us to investigate differences in proliferation of naive and memory CD8+ T cells after BMT. To evaluate the proliferation of these two cell populations after transplant, we injected 0.5×10$^6$ CFSE labeled sorted naive or memory CD8+ T cells from C57BL/6-L2G85 luc+ Thy1.1 mice along with wild type C57BL/6 Thy1.2 TCD BM into irradiated BALB/c mice. We analyzed the rate of cellular division of naive and memory CD8+ T cells in the host spleen on day 3+ after BMT by the change in the intensity of staining for CFSE (FIG. 6D). A representative proliferation assay showed that about 10% of the naive CD8+ T cells and about 5 fold more of memory CD8+ T cells had undergone 2 or fewer cell divisions as determined by the proliferation analysis using Flowjo software. These results are consistent with the MLR data (FIG. 2B) that shows 7 fold less $^3$H-thymidine incorporation of memory versus naive CD8+ T cells after alloantigenic stimulation.

Figure 7:
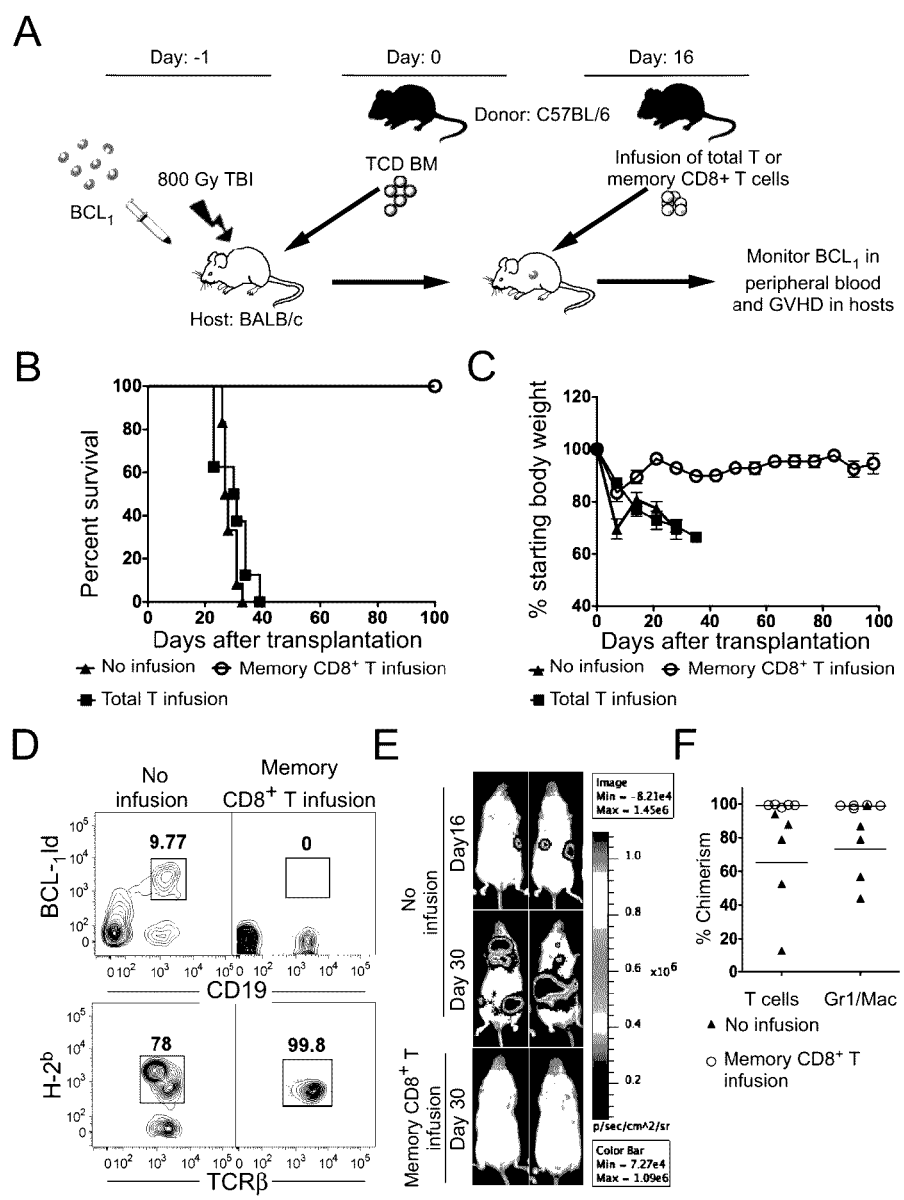
FIG. 7. Survival, weight changes, chimersim, and blood borne $BCL_1$ cells in recipients with progressive tumor growth treated with infusion of total T cells or memory CD8+ T cells. A, Experimental scheme; Lethally irradiated BALB/c recipient mice were injected with 100 $BCL_1$ cells 6 hours after irradiation. Next day (day 0) they received $2\times10^6$ C57BL/6 TCD BM cells (N=10). Day 16 after bone marrow transplant, some mice received an intravenous infusion of $0.5\times10^6$ sorted memory phenotype CD8+ T cells (N=8) or total T cells (N=8). B, Survival of recipients with or without infusion. C, Percentage of starting body weight of host mice given TCD BM with or without infusion as in A. D, Upper panels shows two-color flow cytometric analysis of CD19 versus $BCL_1$-idiotype markers in the peripheral blood from recipients at day 28 after transplant of $2\times10^6$ TCD BM marrow cells with (right panel) or without infusion (left panel). The boxes enclose $BCL_1$ idiotype+ CD19+ cells. Lower panels show representative flow cytometric analysis of peripheral blood at day 28 stained for donor (H-2K$^{b+}$) cells versus TCRβ+ cells among gated TCRβ+ cells. E, Representative examples of BLI of lymphoma growth in mice with or without infusion. After total body irradiation 100 $BCL_1$-luceriferase+ transduced lymphoma cells were injected into BALB/c hosts, followed by injection of $2\times10^6$ TCD-BM on the next day (day 0). Sixteen days after of bone marrow transplant, experimental mice received an infusion of $0.5\times10^6$ memory phenotype CD8+ T cells, and controls received no infusion. Imaging was performed day 16 and day 30 after bone marrow transplant. Two representative mice from each group of 5 mice are shown. F, Percentage of donor type cells among TCRβ+ and Mac1/Gr1+ cells in blood and bone marrow transplant recipients with or without memory cell infusion.

CD8+ Memory T Cells are Effective Treatment for Progressive Lymphoma after BMT. We investigated whether memory CD8+ T cells given as an infusion on day 16 could eradicate BCL$_1$ tumor cells injected with the transplantation of donor TCD BM cells on day 0 (FIG. 7A). Day 16 was chosen for infusion because in preliminary experiments luc+ tumor cells were already expanding in lymphoid tissues of the transplant recipients (FIG. 7E) at that time, but had not yet been detected in blood. In subsequent experiments the hosts were serially monitored for the non-transduced BCL$_1$ tumor in blood and signs of GVHD. All hosts that did not receive the infusion died by day 35 with tumor cells in blood (FIGS. 7B and D). All hosts that received the infusion containing 0.5×10$^6$ memory CD8+ T cells survived over 100 days, (p<0.001), and tumor cells did not appear in the blood (FIGS. 7B and D). The surviving mice in the infusion treated group gained at least 90% of their starting body weight at the end of 100 days, and showed no clinical signs of GVHD (FIG. 7C). When an infusion containing an equal number of total T cells was given instead of CD8+ memory T cells, then all the hosts died by day 40 with clinical signs of GVHD. Weight loss was significantly more than in the CD8+ memory T cell group (p=0.004) (FIGS. 7B and C). The group given the CD8+ memory T cells showed >99% donor T cell chimerism in all hosts whereas the control group without infusion therapy showed mixed donor T cell chimersim (FIG. 7D). FIG. 7F shows that 5 of 5 recipients given infusion therapy were complete chimeras in the T cell lineage and granulocyte/macrophage lineage whereas recipients without the infusion were all mixed chimeras in these lineages. The yield of B cells was too low for accurate determination of B220+ cells. The group given the total T cell infusions that developed lethal GVHD also had >99% T cell chimerism, and $BCL_1$ tumor cells did not appear in blood.

$BCL_1$ lymphoma progression was also assessed by BLI in an additional group of recipients given $BCL_1$-luc$^+$ cells. FIG. 7E shows the lymphoma growth of luciferase expressing $BCL_1$ cells in hosts after TCD BM transplantation with or without memory CD8$^+$ T cell infusion therapy. There was easily detectable lymphoma accumulation in hosts without infusion at day 16, and the tumor progressed at day 30 with increased intensity and extension to additional tissues. In contrast, there was no detectable BLI signal on day 30 in mice that were infused with memory CD8$^+$ T cells.

Previous murine studies showed that memory T cells induce considerably less severe GVHD than naive T cells[9-15]. Accordingly we compared donor total T cells, CD4$^+$ T cells, and CD8$^+$ T cells that had not been separated into purified naive and memory subsets for the induction of lethal GVHD. We also assayed the subsets for anti-$BCL_1$ lymphoma activity in the same MHC mismatched transplant model (C57BL/6→BALB/c) that is most relevant to haplotype mismatched transplantation. Total T cells, naive total T cells, CD4$^+$ T cells and CD8$^+$ T cells induced a significant increase in lethal GVHD as compared to TCD BM alone. Memory total T cells lacked potent anti-tumor activity as compared to memory CD8$^+$ T cells, since 5 fold fewer memory CD8$^+$ T cells induced complete tumor remissions in a higher percentage of recipients than memory total T cells. Accordingly, memory CD8$^+$ T cells became the focus of the study.

In the C57BL/6→BALB/c strain combination, CD4$^+$ total and naive T cells induce considerably more severe GVHD than CD8$^+$ total and CD8$^+$ naive T cells. Whereas 0.5×10$^6$ CD4$^+$ total T cells induced uniformly lethal GVHD by about 30 days, an equal number of CD8$^+$ total T cells induced death in about 40% of the recipients by 75 days. We did not study the graft ant-lymphoma activity of the CD4$^+$ total or naive T cells, since death due to GVHD were considerably more rapid than the appearance of tumor cells in the blood and subsequent tumor associated deaths.

Although memory CD4$^+$ T cells had no in vitro or in vivo alloreactivity, memory CD8$^+$ T cells responded to allogeneic stimulator cells in the current study as judged by proliferation and cytokine secretion. However, the proliferation and IL-2 secretion of the memory cells was significantly reduced (about 7 fold) as compared to the naive cells, but IFN-gamma secretion was significantly increased. Both subsets showed potent killing of allogeneic target cells after initial alloantigenic stimulation. It is unclear why the memory CD8$^+$ T cells were alloreactive whereas in our previous study the memory CD4$^+$ T cells were not. The large majority of memory CD44$^{hi}$CD8$^+$ T cells from untreated mice were central memory T cells, whereas the large majority of memory CD4$^+$ CD44$^{hi}$ T cells were effector memory T cells.

CD8$^+$ CD44$^{hi}$ memory T cells did not induce lethal GVHD in irradiated hosts whereas an equal number of 1×10$^6$ or 0.5×10$^6$ naive CD8$^+$ T cells or total CD8$^+$ T cells, induced lethal GVHD in about 40 to 50% of recipients without tumor cells. Control recipients given TCD BM and $BCL_1$ tumor cells, all died of progressive tumor growth. When the latter recipients were given 0.5×10$^6$ naive or total CD8$^+$ T cells none died from tumor growth. However, about 25% died from GVHD, and the GVHD histopathology scores in the liver, colon, and small intestine of these recipients given naive cells or total CD8$^+$ T cells were significantly increased as compared to recipients given TCD BM cells alone. In contrast, none of the recipients given memory CD8$^+$ CD44$^{hi}$ T cells died during the 100 days observation period, and the GVHD scores were not significantly different from those given TCD BM cells alone. The liver GVHD scores were significantly higher in the hosts given naive as compared to memory CD8$^+$ T cells. The latter result is consistent with a previous report about lack of GVHD with CD8$^+$ CD44$^{hi}$ cells[12], but is different from that reported in a recent study in which purified central memory CD62L$^{hi}$CD44$^{hi}$CD8$^+$ T cells were injected into lethally irradiated MHC mismatched recipients of bone marrow transplants. The central memory CD8$^+$ T cells induced significantly higher GVHD scores than TCD BM controls. A possible explanation is that a combination of central and effector memory CD8$^+$ T cells were used in the current CD8$^+$ CD44$^{hi}$ studies, and that the addition of the effector memory cells attenuated the potency of the GVHD of the central memory T cells. Effector memory T cells have been reported to induce little or no GVHD even after exposure to alloantigens, and regulation of GVHD by this subset has not been studied. Recent studies indicate that CD8$^+$ CD122$^{hi}$ cells T cells that express a memory phenotype have potent regulatory activity.

Both naive and memory CD8$^+$ T cells had the capacity to facilitate the establishment of complete chimerism and tumor eradication despite the lack of GVHD by the memory cells. The increased potency of GVHD of the naive as compared to memory cells was associated with more rapid accumulation and expansion in the lymphoid tissues, liver, and intestines as judged by bioluminescence imaging and CFSE staining. The increased IL-2 secretion of the naive T cells may contribute to the increased early proliferation, and the increased expression of CCR9 and $\alpha_4\beta_7$ integrin gut homing receptors may contribute to the increased naive T cell early trafficking to the intestines.

It is likely that the ability of memory CD8$^+$ T cells to eradicate the tumor cells is dependent on their alloreactivity, since C57BL/6 CD8$^+$ T cells tolerized to BALB/c alloantigens lose their graft anti-tumor activity against $BCL_1$ lymphoma. Alloreactivity of memory CD8$^+$ T cells can be explained by cross reactivity with viral antigens in the environment that have been shown to enhance immune responses to alloantigens on organ transplants. In addition naive CD8$^+$ T cells can masquerade as memory phenotype cells after homeostatic proliferation with maintenance of the naive T cell TCR repertoire.

The current study also investigated CD8$^+$ CD44$^{hi}$ memory and unseparated total T cells as posttransplant infusion therapy in recipients given TCD BM cells and tumor cells at day 0. The infusion was administered at day 16, a time point at which tumor expansion in the lymphoid tissues was apparent by bioluminescence imaging. When unseparated total T cells were used for infusion, then acute lethal GVHD was observed in all recipients. In contrast, purified CD8$^+$ memory T cells allowed for the survival of 100% of the recipients, and survivors remained free of tumor for at least 100 days. The controls given TCD bone marrow without the infusion all succumbed to tumor growth. In conclusion, CD8$^+$ memory T cells containing both central and effector memory subsets were able to separate GVHD and anti-lymphoma activity when added to TCD BM transplants.

What is claimed is:

1. A method of enhancing allogeneic hematopoietic cell transplantation and anti-tumor activity in a human, the method comprising:

preventing cancer relapse by administering to the human previously treated for the cancer with an allogeneic hematopoietic cell transplantation a dose of at least $1 \times 10^6$ and at least 80% pure donor-derived memory $CD8^+$ T cells selected for with an affinity agent specific for CD8, and comprising central and effector memory T cells that are effective to enhance killing of residual cancer cells in the human in the absence of graft versus host disease, wherein the donor-derived memory T cells are selected from $CD8^+CD45RA^-$ and/or $CD8^+CD45RO^+$, wherein the memory $CD8^+$ T cells are administered to the human at least two months after the allogeneic hematopoietic cell transplantation and prior to relapse, and wherein the dose of donor-derived memory T cells enhances complete chimerism.

2. The method of claim 1, wherein the cancer is a lymphoma.

3. The method of claim 1, wherein the cancer is a leukemia.

4. A method of enhancing allogeneic hematopoietic cell transplantation and anti-tumor activity in a human, the method comprising:

preventing cancer relapse by administering to the human previously treated for the cancer with an allogeneic hematopoietic cell transplantation, a dose of at least $1 \times 10^6$ and at least 80% pure, unprimed donor-derived memory T cells selected from $CD8^+CD45RA^-$ and/or $CD8^+CD45RO^+$ selected for with an affinity agent specific for CD8, and comprising central and effector memory T cells that are effective to enhance killing of residual cancer cells in the absence of graft versus host disease in the human, wherein the memory $CD8^+$ T cells are administered to the human at least two months after the allogeneic hematopoietic cell transplantation, wherein the human is treated with a chemotherapeutic or a radiological agent to substantially ablate the hematopoietic system prior to the administration of the dose of donor-derived memory T cells, and wherein the dose of donor-derived memory T cells enhances complete chimerism.

5. The method of claim 1 or 4, wherein the donor-derived $CD8^+CD45RA^-$ and/or $CD8^+CD45RO^+$ memory T cells are collected from the donor of the allogeneic hematopoietic cell transplantation.

6. The method of claim 1 or 4, wherein the donor-derived $CD8^+CD45RA^-$ and/or $CD8^+CD45RO^+$ memory T cells are used directly.

7. The method of claim 1 or 4, wherein the cancer is a hematologic malignancy.

8. The method of claim 1 or 4, wherein the donor-derived $CD8^+CD45RA^-$ and/or $CD8^+CD45RO^+$ memory T cells are frozen or maintained ex vivo in an appropriate culture medium.

9. The method of claim 1 or 4, wherein the human is a pediatric patient.

10. The method of claim 1 or 4, wherein the dose administered to the human is a dose of at least $1 \times 10^8$ and at least 80% pure, unprimed donor-derived $CD8^+CD45RA^-$ and/or $CD8^+CD45RO^+$ memory T cells.

11. The method of claim 10, wherein the human is an adult patient.

12. The method of claim 1 or 4, wherein the human is at least in partial remission from the cancer.

* * * * *